(12) United States Patent
Smith et al.

(10) Patent No.: US 8,192,410 B2
(45) Date of Patent: Jun. 5, 2012

(54) CONTROL DEVICE FOR SURGICAL STOMA

(76) Inventors: Stephen Smith, Cape May Court House, NJ (US); Deborah Smith, Cape May Court House, NJ (US)

( * ) Notice: Subject to any disclaimer, the term of this patent is extended or adjusted under 35 U.S.C. 154(b) by 478 days.

(21) Appl. No.: 12/540,110

(22) Filed: Aug. 12, 2009

(65) Prior Publication Data
US 2010/0042061 A1    Feb. 18, 2010

Related U.S. Application Data

(60) Provisional application No. 61/189,323, filed on Aug. 18, 2008.

(51) Int. Cl.
*A61M 1/00* (2006.01)
(52) U.S. Cl. ......... 604/327; 604/317; 604/322; 604/540
(58) Field of Classification Search ............... 604/32, 604/34, 323, 322, 324, 327
See application file for complete search history.

(56) References Cited

U.S. PATENT DOCUMENTS

| | | | |
|---|---|---|---|
| 4,634,421 | A | 1/1987 | Hegemann |
| 4,804,375 | A | 2/1989 | Robertson |
| 7,258,661 | B2 | 8/2007 | Davies et al. |

*Primary Examiner* — Melanie Hand
(74) *Attorney, Agent, or Firm* — Anderbaum Schloff and Bloom PLLC; Jay Schloff

(57) ABSTRACT

A control device for controlling drainage of waste from a surgical stoma of a human body. The control device comprises a first cylindrical hollow body member, a drain tube extending from the first cylindrical hollow body member, a second cylindrical hollow body member rotatably coupled to the first cylindrical hollow body member and a knob configured on the second cylindrical hollow body member. The first cylindrical hollow body member comprises a skirt portion extending radially outward for being removably attached to a surface surrounding the surgical stoma of the human body. The second cylindrical hollow body member comprises an aperture configured on the second sidewall. A rotation of the knob is capable of aligning the aperture of the second cylindrical hollow body member with the drain tube of the first cylindrical hollow body member thereby forming a passage for draining the waste.

6 Claims, 3 Drawing Sheets

CONTROL DEVICE FOR SURGICAL STOMA

CROSS REFERENCE TO RELATED APPLICATIONS

The present disclosure claims priority under 35 United States Code, Section 119 on the U.S. Provisional Patent Application No. 61/189,323 filed on Aug. 18, 2008, the disclosure of which is incorporated by reference.

FIELD OF THE DISCLOSURE

The present disclosure generally relates to medical prosthetic devices, and, more particularly to a control device for controlling drainage of waste from a surgical stoma of a human body.

BACKGROUND OF THE DISCLOSURE

A surgical stoma is generally referred to an opening created surgically in a human body that connects a body cavity to an outside environment for draining waste such as urine and fecal matter, outside the body cavity. Typically, the surgical stoma is a diverted biological system which involves bisecting intestine or colon portion of gastrointestinal tract and providing an exit for the waste in an abdominal region. Various surgical procedures are known in the art such as colostomy, ileostomy, and the like, for creating surgical stoma. During colostomy, a surgical opening is created in a large intestine of a human body for removal of fecal matter out of the body, bypassing the rectum. Similarly, during ileostomy a surgical opening is created in a small intestine of a human body for removal of intestinal waste.

A pouching system is used for collection of the waste from the surgical stoma. Typically, the pouching system includes a collection bag such as a drain pouch, and the like, and a drainage tube attached to the collection bag. The collection bag is configured to collect waste and the drainage tube is configured to be inserted into a surgical stoma to allow continuous drainage of waste from the surgical stoma into the collection bag. Alternatively, the pouching system may be provided with a mounting plate, commonly referred to as a wafer, for attachment to a surface around the surgical stoma. The mounting plate helps to keep the drainage tube intact on the human body for draining the waste directly into the collection bag. Drainage of the waste from the surgical stoma is involuntary as a user is unable to control the flow of the drainage of the waste and as such has to keep the pouching system attached to the body. However, involuntary drainage of the waste from the surgical stoma into the collection bag may also lead to bursting of the collection bag due to excessive waste collection. Further, uninterrupted use of the pouching system impedes activities of the user such as taking a shower, exercising, and the like and as such the pouching system is inconvenient and uncomfortable for the user.

To address the above, attempts have been made to provide a means for controlling involuntary drainage of waste from the surgical stoma into the collection bag. One such attempt is a use of an occluding device such as a plug. In use, the occluding device blocks the surgical stoma for a period of time. Thereafter, the waste from the surgical stoma is emptied in the collection bag via the drainage tube and the surgical stoma is again occluded with the occluding device. However, the surgically created stoma is incapable of tolerating occlusion for a long period of time and the occlusion may result in pain and discomfort to the user.

Another approach for controlling the drainage of the waste from the surgical stoma includes blocking the drainage tube by twisting the drainage tube. Further, the drainage tube may be blocked with the help of a fastening device, such as a clamp. The drainage tube may be folded and kept collapsed. For draining the waste from the surgical stoma, the drainage tube may be unfolded and connected to the collection bag. However, such twisting, folding and collapsing of the drainage tube may affect the structural integrity of the tube, and, as such, leakage of the waste from the surgical stoma may take place prior to the collection in the collection bag.

Further, the conventional methods known in the art for draining waste from the surgical stoma are incapable of allowing gases produced in a body of the user to exit. Accumulation of the gases in the body of the user may lead to severe medical complications for the user. Also, the gases accumulated in the body of the user may cause bursting of the collection bag and/or leakage in the drainage tube.

Accordingly, there exists a need to preclude involuntary drainage of waste from a surgical stoma. Further, there exists a need to control drainage of waste from a surgical stoma without compromising the health, safety and comfort of a user. Furthermore, there exists a need for an easy and efficient way of releasing gases produced in a body of a user having a surgical stoma.

SUMMARY OF THE DISCLOSURE

In view of the foregoing disadvantages inherent in the prior art, the general purpose of the present disclosure is to provide a control device for a surgical stoma, to include all the advantages of the prior art and to overcome the drawbacks inherent therein.

Accordingly, an object of the present disclosure is to preclude involuntary drainage of waste from a surgical stoma.

Another object of the present disclosure to control drainage of waste from a surgical stoma without compromising health, safety and comfort of a user.

Yet another object of the present disclosure is to provide an easy and efficient way of releasing gases produced in a body of a user having a surgical stoma.

In light of the above objects, in one aspect of the present disclosure, a control device for a surgical stoma is provided. The control device comprises a first cylindrical hollow body member, a drain tube, a second cylindrical hollow body member and a knob. The first cylindrical hollow body member comprises a first sidewall, a first open end portion and a second open end portion. The first cylindrical hollow body member further comprises a skirt portion extending radially outward from the first open end portion. The skirt portion is capable of being removably attached to a surface surrounding the surgical stoma of the human body. The drain tube extends outward from the first sidewall of the first cylindrical hollow body member. The second cylindrical hollow body member is rotatably coupled to the first cylindrical hollow body member. The second cylindrical hollow body member comprises a second sidewall, a proximal closed end portion and a distal open end portion configuring a cavity. The second cylindrical hollow body member further comprises an aperture configured on the second sidewall. The knob is configured on the proximal closed end portion of the second cylindrical hollow body member. The second cylindrical hollow body member is disposed in the first cylindrical hollow body member to align the second sidewall of the second cylindrical hollow body member with the first sidewall of the first cylindrical hollow body member for rotatably coupling the second cylindrical hollow body member to the first cylindrical hollow body member. The rotation of the knob in at least one direction is capable of rotating the second cylindrical hollow body member with respect to the first cylindrical hollow body member to align the aperture of the second cylindrical hollow body member with the drain tube of the first cylindrical hollow body member thereby forming a passage for draining the waste from the surgical stoma of the human body.

Further, the drain tube is capable of attaching to a collection bag for collecting the waste drained from the surgical stoma. The rotation of the knob in at least one direction is capable of rotating the second cylindrical hollow body member with respect to the first cylindrical hollow body member such that the control device assumes at least one of an open position and a closed position. In the open position of the control device, the waste is drained from the control device via the drain tube into the collection bag. In the closed position, involuntary drainage of the waste from a surgical stoma is precluded.

In another aspect of the present disclosure, a control device including a relief valve is provided. The relief valve is configured to relieve gas pressure produced during the digestion process inside a body of a user having a surgical stoma.

These together with other aspects of the present disclosure, along with the various features of novelty that characterize the present disclosure, are pointed out with particularity in the claims annexed hereto and form a part of this present disclosure. For a better understanding of the present disclosure, its operating advantages, and the specific objects attained by its uses, reference should be made to the accompanying drawing and descriptive matter in which there are illustrated exemplary embodiments of the present disclosure.

BRIEF DESCRIPTION OF THE DRAWINGS

The advantages and features of the present disclosure will become better understood with reference to the following detailed description and claims taken in conjunction with the accompanying drawing, in which:

Like reference numerals refer to like parts throughout the description of several views of the drawings.

DETAILED DESCRIPTION OF THE DISCLOSURE

The exemplary embodiments described herein detail for illustrative purposes are subject to many variations in structure and design. It should be emphasized, however, that the present disclosure is not limited to a control device for a surgical stoma as shown and described. It is understood that various omissions and substitutions of equivalents are contemplated as circumstances may suggest or render expedient, but these are intended to cover the application or implementation without departing from the spirit or scope of the claims of the present disclosure. Also, it is to be understood that the phraseology and terminology used herein is for the purpose of description and should not be regarded as limiting.

The terms, "first," "second," and the like, herein do not denote any order, elevation or importance, but rather are used to distinguish placement of one element over another. Further, the terms, "a" and "an" herein do not denote a limitation of quantity, but rather denote the presence of at least one of the referenced item.

The term "waste" used herein, includes urine and fecal matter in a liquid form.

The present disclosure provides a control device for controlling drainage of waste from a surgical stoma. The control device is capable of adhering to a surface surrounding a surgical stoma of a user for controlling involuntary drainage of waste from the surgical stoma. Further, the control device allows the user to engage in various activities such as exercise, bathing, working, and the like, without any fear of leakage of the waste from the surgical stoma. The control device controls the drainage of waste from the surgical stoma without compromising the health, safety and comfort of the user. Additionally, the control device provides for easy and efficient way of exiting gases produced in the body of the user having the surgical stoma.

Figure 1:
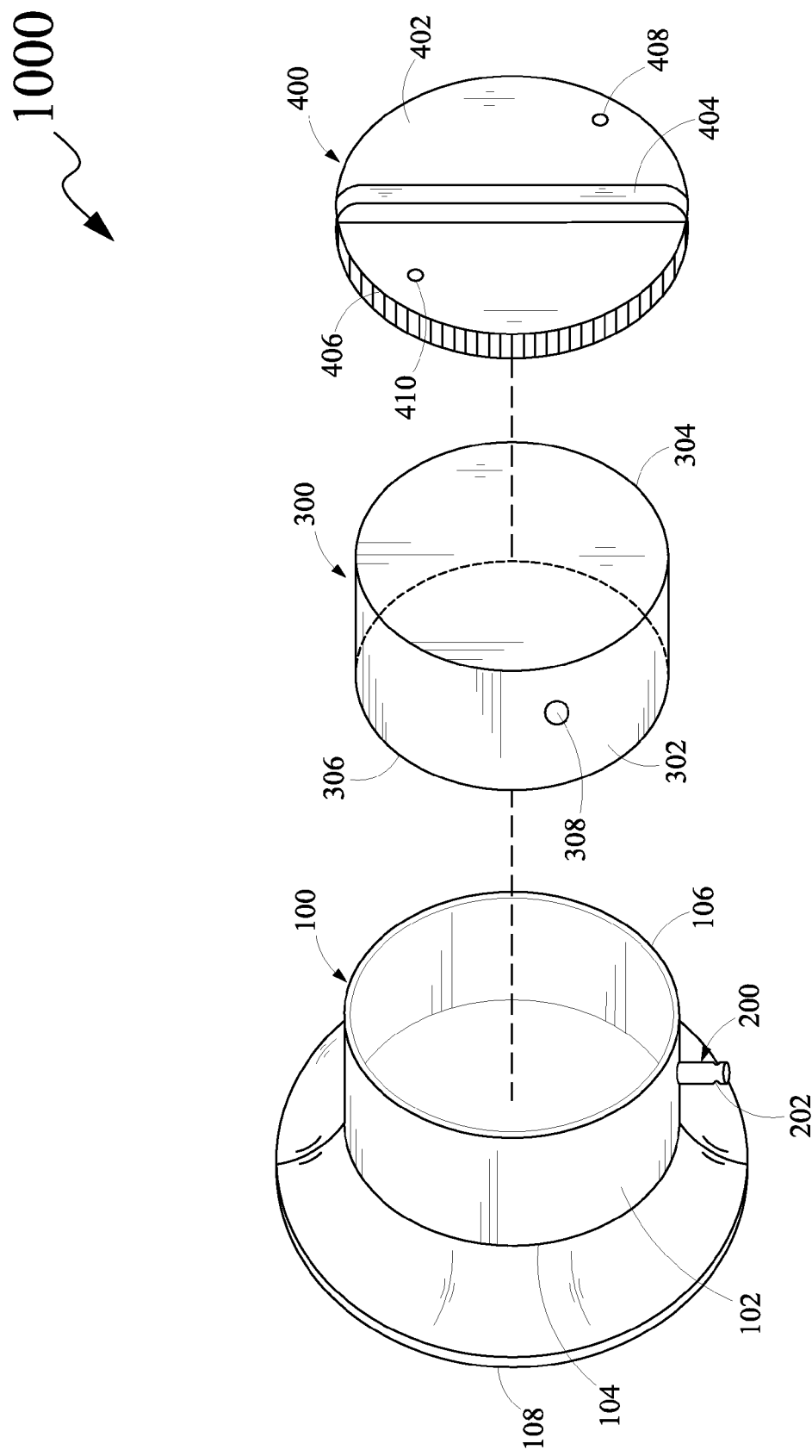
FIG. 1 illustrates an exploded view of a control device for a surgical stoma, in accordance with an embodiment of the present disclosure.
Figure 2:
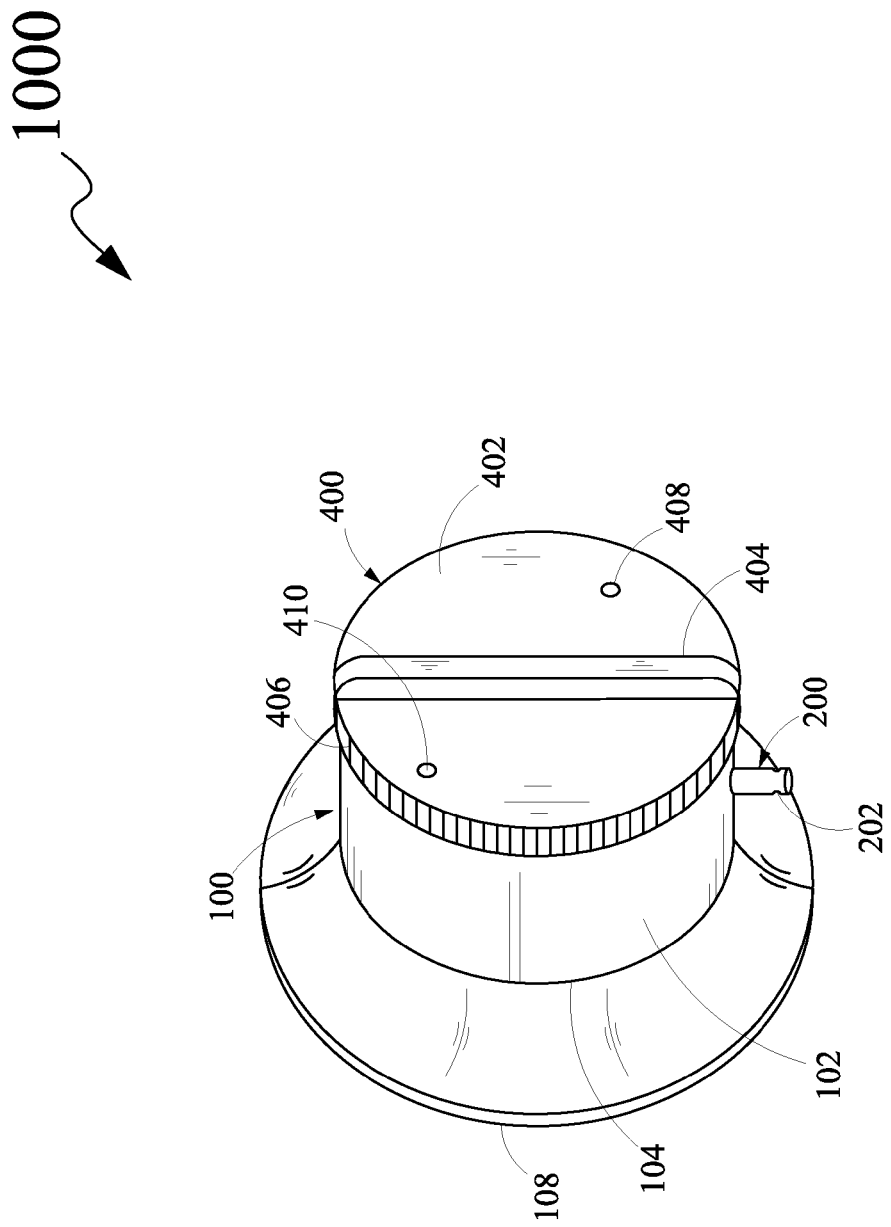
FIG. 2 illustrates an assembled view of the control device of FIG. 1.

Referring to FIGS. 1 and 2, a control device 1000 is illustrated, in accordance with an embodiment of the present disclosure. More specifically, FIG. 1 illustrates an exploded view of the control device 1000 and FIG. 2 illustrates an assembled view of the control device 1000. The control device 1000 is capable of controlling drainage of waste from a surgical stoma (not shown) of a human body (not shown). The control device 1000 includes a first cylindrical hollow body member 100, a drain tube 200 extending from the first cylindrical hollow body member 100, a second cylindrical hollow body member 300 rotatably coupled with the first cylindrical hollow body member 100 and a knob 400 configured on the second cylindrical hollow body member 300.

The first cylindrical hollow body member 100 includes a first sidewall 102, a first open end portion 104 and a second open end portion 106 opposite to the first open end portion 104. Further, the first cylindrical hollow body member 100 includes a skirt portion 108 extending radially outward from the first open end portion 104. The skirt portion 108 is configured to be removably attached on a surface (not shown) surrounding the surgical stoma of the human body. More specifically, the skirt portion 108 includes a self adhesive tape (not shown) configured thereon for removably attaching to the surface surrounding the surgical stoma of the human body. The self adhesive tape may be a medically acknowledged peel-off self adhesive tape, such that the self adhesive tape is safe for attachment to the human body. However, it will be evident to a person skilled in the art that the self adhesive tape for adhering to the surface surrounding the surgical stoma is disclosed for exemplary purpose and as such may not be construed as limiting. Further, the skirt portion 108 may include a layer of wax (not shown) coated thereon. The wax prevents the skin surrounding the surgical stoma from coming in contact with the waste, thereby protecting the skin from infections, itching, burning and the like.

The drain tube 200 extends outward from the first sidewall 102 of the first cylindrical hollow body member 100. The drain tube 200 is a tubular structure with first end (not shown) attached to the first sidewall 102 of the first cylindrical hollow body member 100 and the second end (not numbered) capable of removably attaching to an opening (not shown) of a collection bag (not shown). The first end of the drain tube 200 configured with the first sidewall 102 of the first cylindrical hollow body member 100 includes an opening (not shown), thereby providing an exit for the waste from the surgical stoma. Further, the second end of the drain tube 200 may include a notch 202 for firmly attaching the drain tube 200 with the opening of the collection bag in a snap fit manner. Furthermore, size and diameter of the drain tube 200 may be configured in a manner such that the drain tube 200 is capable of attaching to any collection bag of standard size. In an embodiment of the present disclosure, the drain tube 200 and the first cylindrical hollow body member 100 are integrally configured with each other by a manufacturing process, such as molding to form a single unitary structure. However, it will be evident to the person skilled in the art that the drain tube 200 and the first cylindrical hollow body member 100 may be a single unitary structure or a separate components attached together by any conventional means known in the art.

The second cylindrical hollow body member 300 includes a second sidewall 302, a proximal closed end portion 304 and a distal open end portion 306 opposite to the proximal closed end portion 304. The second sidewall 302, the proximal closed end portion 304 and the distal open end portion 306 configure a cavity (not numbered). Further, the second cylindrical hollow body member 300 includes an aperture 308 configured on the second sidewall 302.

The second cylindrical hollow body member 300 is rotatably coupled to the first cylindrical hollow body member 100. More specifically, the second cylindrical hollow body member 300 is disposed in the first cylindrical hollow body member 100 in a manner such that the second sidewall 302 of the second cylindrical hollow body member 300 aligns with the first sidewall 102 of the first cylindrical hollow body member 100 to ensure a snuggest fit. In an embodiment of the present disclosure, the first sidewall 102 of the first cylindrical hollow body member 100 may be provided with notches (not shown) and the second sidewall 302 of the second cylindrical hollow body member 300 may be provided with corresponding grooves (not shown) in order to keep the second cylindrical hollow body member 300 aligned in the first cylindrical hollow body member 100. Further, such an alignment of the second sidewall 302 of the second cylindrical hollow body member 300 with the first sidewall 102 of the first cylindrical hollow body member 100 is capable of allowing the second cylindrical hollow body member 300 to rotate freely within the first cylindrical hollow body member 100. On rotating the second cylindrical hollow body member 300 in at least one direction with respect to the first cylindrical hollow body member 100, the aperture 308 of the second cylindrical hollow body member 300 aligns with the opening of the drain tube 200 thereby providing a passage for the drainage of the waste from the surgical stoma to the collection bag. In an embodiment of the present disclosure, the diameter of the aperture 308 on the second sidewall 302 is similar to diameter of the opening of the drain tube 200.

Further, the knob 400 is configured on the proximal closed end portion 304 of the second cylindrical hollow body member 300. The knob 400 includes a circular dial member 402 and a longitudinal protuberance 404 running across the diameter of the circular dial member 402. The longitudinal protuberance 404 is capable of indicating positioning of the knob 400. The circular dial member 402 includes a grippable peripheral portion 406 for rotating the knob 400. In an embodiment of the present disclosure, the knob 400 may be integrally configured with the second cylindrical hollow body member 300 by a manufacturing process, such as molding, to form a single unitary structure. In another embodiment of the present disclosure, the knob 400 and the second cylindrical hollow body member 300 may be configured as separate components joined together by conventional methods known in the art. On placing the second cylindrical hollow body member 300 in the first cylindrical hollow body member 100, the knob 400 configured on the proximal closed end portion 304 of the second cylindrical hollow body member 300 rests on the second open end portion 106 of the first cylindrical hollow body member 100.

Furthermore, rotation of the knob 400 with the help of the grippable peripheral portion 406 in at least one direction is capable of rotating the second cylindrical hollow body member 300 with respect to the first cylindrical hollow body member 100. The rotation of the second cylindrical hollow body member 300 with respect to the first cylindrical hollow body member 100 in the at least one direction is adapted to allow the control device 1000 to assume at least one of an open position and a closed position. The longitudinal protuberance 404 is capable of indicating the at least one of the open position and the closed position of the control device 1000. In the open position of the control device 1000, the aperture 308 of the second cylindrical hollow body member 300 is capable of aligning with the opening of the drain tube 200 of the first cylindrical hollow body member 100. More specifically, the aligning of the aperture 308 with the opening of the drain tube 200 configures a passage which allows drainage of the waste from the surgical stoma. In the closed position of the control device 1000, the aperture 308 of the second cylindrical hollow body member 300 is in non alignment with the opening of the drain tube 200 of the first cylindrical hollow body member 100. More specifically, the non alignment of the aperture 308 with the opening of the drain tube 200 causes blockage of the opening of the drain tube 200 and as such the surgical stoma is stopped from releasing waste thereby controlling involuntary drainage of waste from the surgical stoma into the collection bag.

The control device 1000 includes a relief valve 408 configured on the knob 400, extending into the cavity of the second cylindrical hollow body member 300. The relief valve 408 is an air pressure relief valve configured to remove gas pressure. More specifically, the relief valve 408 is capable of relieving a pressure developed by gases produced during digestion process inside the human body. In an embodiment of the present disclosure, the control device 1000 includes a flush port 410 configured on the knob 400 extending into the cavity of the second cylindrical hollow body member 300. The flush port 410 may be configured on the knob 400 for cleansing the surgical stoma. The flush port 410 may be configured to connect with a water source (not shown) which provides a sprinkle of water in order to clean the surgical stoma after the waste have been drained from the surgical stoma.

The first cylindrical hollow body member 100, the drain tube 200, the second cylindrical hollow body member 300 and the knob 400 are made of medically acknowledged safe materials. In an embodiment of the present disclosure, the first cylindrical hollow body member 100, the drain tube 200, the second cylindrical hollow body member 300 and the knob 400 are made of durable plastic material. In another embodiment of the present disclosure, the first cylindrical hollow body member 100, the drain tube 200, the second cylindrical hollow body member 300 and the knob 400 are made of silicone. However, it will be evident to those skilled in the art that any other durable material known in the art may be utilized for configuring the control device 1000.

Figure 3:
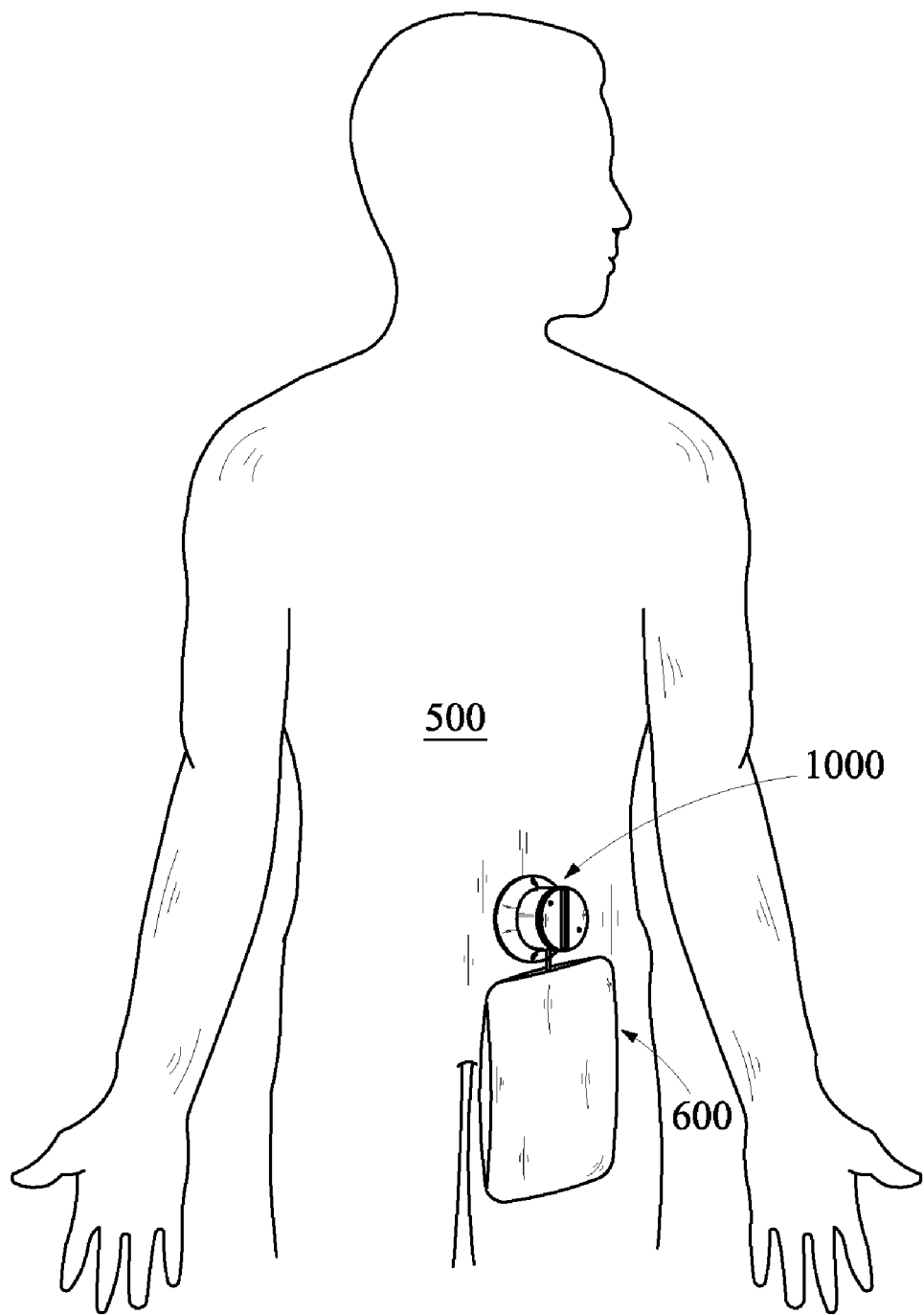
FIG. 3 illustrates a perspective view of a control device attached to a human body for draining waste into a collection bag, in accordance with an exemplary embodiment of the present disclosure.

The control device 1000 of the present disclosure may be of different shapes. In an embodiment of the present disclosure (as shown in FIGS. 1 to 3), the skirt portion 108 extending radially from the first cylindrical hollow body member 100 is circular in shape. In another embodiment of the present disclosure the skirt portion 108 is square in shape. However, it will be evident to those skilled in the art to use any other shape for the configuration of the skirt portion 108. Also, the control device 1000 of the present disclosure may be of different sizes depending on the size of the surgical stoma. In an embodiment of the present disclosure, the control device 1000 may be of about 3½ inches in diameter. However, it will be evident to those skilled in art that the control device 1000 may be of any size suitable to cover the surgical stoma.

Now referring to FIG. 3, a perspective view of the control device 1000 attached to a human body 500 for draining waste to a collection bag, such as a drain pouch 600, is illustrated in accordance with an exemplary embodiment of the present disclosure.

In use, the control device 1000 is adhered to a surface surrounding the surgical stoma. More specifically, the self adhesive tape of the skirt portion 108 is capable of attaching to the surface surrounding the surgical stoma. The drain tube 200 extending outward from the first sidewall 102 of the first cylindrical hollow body member 100 is capable of removably attaching to the drain pouch 600. More specifically, the drain tube 200 is capable of attaching in a snap fit manner to an opening (not shown) of the drain pouch 600. However, it will be evident to those skilled in the art that the attachment of the drain pouch 600 with the drain tube 200 is disclosed for exemplary purpose and as such may not be considered as limiting. The collection bag such as the drain pouch 600 may be a standard collection bag employed to collect waste from the surgical stoma.

Further, when the knob 400 is rotated in the at least one direction, for instance in a clockwise direction, by gripping the grippable peripheral portion 406 to assume the open position of the control device 1000, the aperture 308 of the second cylindrical hollow body member 300 comes in alignment with the opening of the drain tube 200 of the first cylindrical hollow body member 100. Once the control device 1000 assumes the open position, the waste may be drained from the surgical stoma to the drain pouch 600. After the waste has been emptied into the drain pouch 600, the knob 400 may be rotated in the at least one direction, for instance in an anticlockwise direction, to assume the closed position. In the closed position, the aperture 308 of the second cylindrical hollow body member 300 is moved away from the opening of the drain tube 200 of the first cylindrical hollow body member 100 such that the opening of the drain tube 200 is blocked. Once the control device 1000 assumes the closed position, the control device 1000 restricts drainage of the waste from the surgical stoma and as such the drain pouch 600 may be detached from the drain tube 200.

A control device, such as the control device 1000, as described herein, offers the following advantages. The control device is capable of controlling the drainage of the waste from the surgical stoma of the human body. Rotation of the knob in at least one direction is capable of rotating the second cylindrical hollow body member with respect to the first cylindrical hollow body member such that the control device assumes at least one of the open position and the closed position of the control device. In the open position of the control device, the control device is capable of draining the waste from the surgical stoma into the collection bag attached to the control device. In the closed position of the control device, the control device is configured to preclude involuntary drainage of the waste from the surgical stoma and as such allowing a user of the control device to engage in various activities such as exercise, bathing, working, and the like, without any fear of leakage of the waste from the surgical stoma. Further, a relief valve, such as the relief valve 408, helps to relieve the gas pressure developed in the human body from the surgical stoma. Controlled drainage of the waste from the surgical stoma to the collection bag provides hygienic condition for the user and as such the control device is safe and comfortable to the user. Furthermore, cleansing the surgical stoma with water through a flush port, such as the flush port 410, after the drainage of the waste helps to provide a clean and hygienic environment and as such prevents infection of the surgical stoma. Moreover, the easy attachment and removal of the collection bag from the control device provides an easy and efficient way of handling and disposal of the waste from the surgical stoma.

The foregoing descriptions of specific embodiments of the present disclosure have been presented for purposes of illustration and description. They are not intended to be exhaustive or to limit the present disclosure to the precise forms disclosed, and obviously many modifications and variations are possible in light of the above teaching. The embodiments were chosen and described in order to best explain the principles of the present disclosure and its practical application, to thereby enable others skilled in the art to best utilize the present disclosure and various embodiments with various modifications as are suited to the particular use contemplated. It is understood that various omission and substitutions of equivalents are contemplated as circumstance may suggest or render expedient, but such are intended to cover the application or implementation without departing from the spirit or scope of the claims of the present disclosure.

What is claimed is:

1. A control device for controlling drainage of waste from a surgical stoma of a human body, the control device comprising:

a first cylindrical hollow body member having a first sidewall, a first open end portion and a second open end portion, the first cylindrical hollow body member comprising a skirt portion extending radially outward from the first open end portion capable of being removably attached to a surface surrounding the surgical stoma of the human body;

a drain tube extending outward from the first sidewall of the first cylindrical hollow body member;

a second cylindrical hollow body member rotatably coupled to the first cylindrical hollow body member, the second cylindrical hollow body member having a second sidewall, a proximal closed end portion and a distal open end portion configuring a cavity, the second cylindrical hollow body member comprising an aperture configured on the second sidewall; and a knob configured on the proximal closed end portion of the second cylindrical hollow body member, wherein the second cylindrical hollow body member is disposed in the first cylindrical hollow body member to align the second sidewall of the second cylindrical hollow body member with the first sidewall of the first cylindrical hollow body member for rotatably coupling the second cylindrical hollow body member to the first cylindrical hollow body member, and, wherein a rotation of the knob in at least one direction is capable of rotating the second cylindrical hollow body member with respect to the first cylindrical hollow body member to align the aperture of the second cylindrical hollow body member with the drain tube of the first cylindrical hollow body member thereby forming a passage for draining the waste from the surgical stoma of the human body.

2. The control device of claim 1, wherein the skirt portion comprises a self adhesive tape for removably attaching to the surface surrounding the surgical stoma of the human body.

3. The control device of claim 1 further comprising a relief valve configured on the knob for relieving gas pressure developed in the human body.

4. The control device of claim 1 further comprising a flush port configured on the knob for cleansing the surgical stoma.

5. The control device of claim 1, wherein the drain tube is capable of being attached to a collection bag.

6. The control device of claim 1, wherein the knob comprises a grippable peripheral portion.

\* \* \* \* \*